(12) United States Patent
Nilsson et al.

(10) Patent No.: US 9,180,593 B2
(45) Date of Patent: Nov. 10, 2015

(54) ANALYSER FOR OPTICAL ANALYSIS OF A BIOLOGICAL SPECIMEN

(75) Inventors: Jan Nilsson, Lund (SE); Hans Bengtsson, Eslöv (SE); Ragnar Segersten, Ängelholm (SE); Conny Gillström, Karlskoga (SE)

(73) Assignee: Cella Vision AB, Lund (SE)

( * ) Notice: Subject to any disclaimer, the term of this patent is extended or adjusted under 35 U.S.C. 154(b) by 564 days.

(21) Appl. No.: 12/737,699

(22) PCT Filed: Dec. 18, 2009

(86) PCT No.: PCT/EP2009/067528
§ 371 (c)(1),
(2), (4) Date: Mar. 23, 2011

(87) PCT Pub. No.: WO2010/076244
PCT Pub. Date: Jul. 8, 2010

(65) Prior Publication Data
US 2011/0304722 A1 Dec. 15, 2011

Related U.S. Application Data

(60) Provisional application No. 61/193,839, filed on Dec. 30, 2008.

(30) Foreign Application Priority Data

Dec. 30, 2008 (EP) ..................................... 08173064

(51) Int. Cl.
*H04N 7/18* (2006.01)
*B25J 9/12* (2006.01)
*G01N 35/00* (2006.01)

(52) U.S. Cl.
CPC ........... *B25J 9/123* (2013.01); *G01N 35/00029* (2013.01); *G01N 35/0099* (2013.01); *G01N 2035/00039* (2013.01); *Y10T 74/20317* (2015.01)

(58) Field of Classification Search
USPC .............................. 348/79, 80; 359/362–435
See application file for complete search history.

(56) References Cited

U.S. PATENT DOCUMENTS

| 3,086,743 A | 4/1963 | Littmann |
| 3,132,200 A * | 5/1964 | Muller et al. ................. 359/379 |

(Continued)

FOREIGN PATENT DOCUMENTS

| DE | 4113279 | 10/1992 |
| DE | 10030772 | 10/2001 |

(Continued)

OTHER PUBLICATIONS

English Translation of Japanese Office Action for Application No. 2011-533773 dated Sep. 25, 2012.

(Continued)

*Primary Examiner* — Sath V Perungavoor
*Assistant Examiner* — Dakshesh Parikh
(74) *Attorney, Agent, or Firm* — Harness, Dickey and Pierce, P.L.C.

(57) ABSTRACT

An analyzer is disclosed for optical analysis of a biological specimen. In at least one embodiment, the analyzer includes optics which includes a camera, intermediate optics and front optics. The intermediate optics is movably arranged and the front optics is fixedly arranged. An analyzer for optical analysis of a biological specimen, in at least one embodiment includes a robot for transporting a slide to be analyzed. The robot is controlled by at least three motors to allow movement of the robot in three dimensions. The robot includes a handling device configured to grip the slide.

11 Claims, 4 Drawing Sheets

(56) References Cited

U.S. PATENT DOCUMENTS

| | | | |
|---|---|---|---|
| 3,514,595 A * | 5/1970 | Schwarz | 250/311 |
| 4,248,498 A | 2/1981 | Georges | |
| 4,367,915 A | 1/1983 | Georges | |
| 4,852,985 A | 8/1989 | Fujihara et al. | |
| 5,136,429 A * | 8/1992 | Bergner et al. | 359/663 |
| 5,144,478 A * | 9/1992 | Toshimitsu | 359/392 |
| 5,360,977 A * | 11/1994 | Onuki et al. | 850/6 |
| 5,825,535 A | 10/1998 | Biber et al. | |
| 6,094,299 A | 7/2000 | Schau et al. | |
| 6,151,161 A | 11/2000 | Mayer et al. | |
| 6,157,495 A * | 12/2000 | Kawasaki | 359/686 |
| 6,226,118 B1 * | 5/2001 | Koyama et al. | 359/380 |
| 6,268,957 B1 * | 7/2001 | Hoover et al. | 359/368 |
| 6,285,498 B1 | 9/2001 | Mayer | |
| 6,348,964 B1 | 2/2002 | Wagner et al. | |
| 6,396,532 B1 | 5/2002 | Hoover et al. | |
| 6,437,913 B1 * | 8/2002 | Kishi | 359/389 |
| 6,473,230 B2 | 10/2002 | Hedrich | |
| 6,525,876 B1 | 2/2003 | Gilbert et al. | |
| 6,674,575 B1 | 1/2004 | Tandler et al. | |
| 6,720,558 B2 * | 4/2004 | Kaneyama | 250/311 |
| 6,795,239 B2 | 9/2004 | Tandler et al. | |
| 6,813,071 B2 * | 11/2004 | Takahama | 359/381 |
| 6,847,481 B1 | 1/2005 | Ludl et al. | |
| 6,850,362 B2 * | 2/2005 | Brooker | 359/379 |
| 6,905,300 B1 | 6/2005 | Russum | |
| 6,917,377 B2 * | 7/2005 | Aizaki et al. | 348/79 |
| 6,924,930 B2 | 8/2005 | Uhl | |
| 7,023,614 B2 | 4/2006 | Gilbert | |
| 7,140,738 B2 | 11/2006 | Guiney et al. | |
| 7,245,425 B2 * | 7/2007 | Miyashita | 359/384 |
| 7,248,403 B2 * | 7/2007 | Nakagawa | 359/380 |
| 7,362,511 B2 * | 4/2008 | Suzuki | 359/687 |
| 7,387,385 B2 * | 6/2008 | Sander | 351/206 |
| 7,630,113 B2 * | 12/2009 | Sase et al. | 359/212.1 |
| 8,098,279 B2 | 1/2012 | Sase et al. | 348/79 |
| 8,395,855 B2 * | 3/2013 | Topliss | 359/823 |
| 2001/0028497 A1 | 10/2001 | Uhl | |
| 2002/0001126 A1 | 1/2002 | Engelhardt | |
| 2002/0131166 A1 | 9/2002 | Woo et al. | |
| 2002/0135870 A1 | 9/2002 | Hedrich | |
| 2002/0149845 A1 | 10/2002 | Mayer | |
| 2002/0176160 A1 * | 11/2002 | Suzuki et al. | 359/380 |
| 2003/0082516 A1 | 5/2003 | Straus | |
| 2003/0143580 A1 | 7/2003 | Straus | |
| 2003/0165011 A1 | 9/2003 | Tandler et al. | |
| 2003/0170613 A1 | 9/2003 | Straus | |
| 2003/0227562 A1 * | 12/2003 | Gouch et al. | 348/345 |
| 2004/0066553 A1 | 4/2004 | Gilbert | |
| 2004/0072225 A1 | 4/2004 | Rollins et al. | |
| 2004/0136868 A1 | 7/2004 | Bevirt et al. | |
| 2004/0165694 A1 * | 8/2004 | Yonetani et al. | 378/5 |
| 2004/0262162 A1 * | 12/2004 | Roach et al. | 204/600 |
| 2005/0111088 A1 * | 5/2005 | Winterot et al. | 359/368 |
| 2005/0225851 A1 | 10/2005 | Koerner et al. | |
| 2005/0248837 A1 * | 11/2005 | Sase et al. | 359/380 |
| 2006/0109432 A1 | 5/2006 | Guiney et al. | |
| 2006/0228107 A1 * | 10/2006 | Takamatsu et al. | 396/432 |
| 2006/0238765 A1 | 10/2006 | Shah et al. | |
| 2007/0053058 A1 | 3/2007 | Angelini et al. | |
| 2007/0057106 A1 | 3/2007 | Scampini | |
| 2008/0020128 A1 * | 1/2008 | van Ryper et al. | 427/2.11 |
| 2009/0195646 A1 * | 8/2009 | Ganser et al. | 348/79 |

FOREIGN PATENT DOCUMENTS

| | | | |
|---|---|---|---|
| DE | 10246275 | 4/2004 | |
| DE | 102004017694 | 9/2005 | |
| EP | 1150154 | 10/2001 | |
| EP | 1611472 | 1/2006 | |
| JP | 05345247 | 12/1993 | |
| JP | 06113570 | 4/1994 | |
| JP | 08313785 | 11/1996 | |
| JP | 8327911 | 12/1996 | |
| JP | 10148247 | 6/1998 | |
| JP | 11083687 | 3/1999 | |
| JP | 2003215461 | 7/2003 | |
| JP | 2005292725 A | 10/2005 | |
| JP | 2005-321657 | 11/2005 | G02B 21/00 |
| JP | 2006-337925 | 12/2006 | G02B 21/06 |
| JP | 2007-133435 | 5/2007 | G02B 21/06 |
| WO | WO-9612170 A1 | 4/1996 | |
| WO | WO 9921042 | 4/1999 | |
| WO | WO 2004070366 | 8/2004 | |
| WO | WO 2004088387 | 10/2004 | |
| WO | WO 2006072886 | 7/2006 | |
| WO | WO 2008069220 A1 * | 6/2008 | |

OTHER PUBLICATIONS

Dietz, P. et al., "A Compact Scanning Tunnel Microscope," Ultramircoscopy 25, pp. 107-110, Mar. 23, 2011.

Hohmann-Marriott, M.F. et al., "Digital Position Determination System for Electron Microscopy," Microscopy Research and Technique, pp. 106-111, 2005.

Potter, C. S. et al., "Robotic grid loading system for a transmission electron microscope," Journal of Structural Biology, pp. 431-440, 2004.

Wang, C. et al., "Computer-controlled optical scanning tile microscope," Applied Optics, vol. 45, No. 6, pp. 1148-1152, Feb. 20, 2006.

* cited by examiner

ANALYSER FOR OPTICAL ANALYSIS OF A BIOLOGICAL SPECIMEN

This application is a National Phase entry of PCT Application number PCT/EP2009/067528 filed on Dec. 18, 2009, which claims priority under 35 U.S.C. §119 to EP 08173064.0 filed on Dec. 30, 2008 and under 35 U.S.C. 61/193,839, filed on Dec. 30, 2008, the entire contents of each of which are hereby incorporated herein by reference.

TECHNICAL FIELD

The present invention relates to an analyser for optical analysis of a biological specimen, comprising a robot for transporting a slide with a sample to be analysed. The present invention also relates to an analyser for optical analysis of a biological specimen, comprising optics which comprises a camera, intermediate optics and front optics. It should be noted that the robot and the optics of the analyser described can be used together in an analyser, but that they can also be used independently of each other.

BACKGROUND ART

Computer aided image analysis of biological material has become increasingly popular during the last years. For instance computer-aided processes for counting and classifying white blood cells in blood smears and body fluids have been developed. These types of analyses constitute an important step in diagnosing infections, allergies, or blood cancers.

In microscopic analyses of various medical preparations, for instance the analysis of a blood sample, a cytology sample, or a pathology sample, it is possible to use automatic scanning microscope systems. One example of such a microscope system is CellaVision DM 96 from CellaVision AB, which is used for localisation and pre-classification of the various types of white blood cells in peripheral blood smears. This system also pre-characterises parts of the red morphology and provides functionality for platelet estimation. The system scans a blood sample which is smeared onto a microscope slide. During scanning, the microscope system is making controlled positioning movements of the microscope slide in two directions, which can be referred to as directions in the x,y-plane. The microscope slide is placed on a table that moves in the two directions by means of two rails and a ball screw per direction.

A crucial part of such a system is to have a controlled handling of the sample. The sample, which is placed on a microscope slide, is to be trans-ported from a cassette to the microscope where a coarse adjustment as well as a fine adjustment of focus is made to achieve a satisfying image of the blood sample. Several devices for loading slides from a cassette onto a stage of a microscope are known.

U.S. Pat. No. 6,847,481 discloses an automated slide loader cassette for a microscope. The automated slide loader comprises a slide cassette indexer for containing a plurality of microscope slides, a slide exchange arm for gripping a microscope slide within the indexer and for transporting the slide to a microscope for observation and then back to the indexer, and an x,y-stage for moving the slide exchange arm between the indexer and the microscope and positioning the slide for analysis.

There are problems associated with assuring that the two rails are perfectly parallel, and if they are not, the table will not be able to move properly.

SUMMARY OF THE INVENTION

It is an object of the present invention to provide an improvement of the above techniques and prior art.

More particularly, it is an object of the present invention to provide an analyser having a robot for transporting a slide with a sample to be analysed that is movable in three dimensions and can be used to obtain focus of the sample without moving the optics in the analyser.

It is a further object of the present invention to provide an analyser comprising optics comprising a camera, intermediate optics and front optics, wherein the intermediate optics is movably arranged and the front optics is fixedly arranged.

These and other objects as well as advantages that will be apparent from the following description of the present invention are achieved by an analyser comprising optics according to independent claim 1 and an analyser comprising a robot according to independent claim 10.

The analyser thus comprises optics comprising a camera, intermediate optics and front optics, wherein the intermediate optics is movably arranged and the front optics is fixedly arranged. This is advantageous in that a number of different magnification factors can be achieved. Further, with some choices of objectives, the intermediate optics may be less sensitive to faults in the positioning than the front optics, thereby making it advantageous to arrange the front optics fixed.

The optics may comprise one or more movably arranged light sources. Since the light source is movable, it can be moved when the slide is removed from the microscope, thereby making it possible to move the slide far enough away from the front optics to release optical oil placed on the slide from the front optics. Otherwise, there is a risk that optical oil from the slide soils the light source.

The light source may be an LED. An LED requires less power than a regular light bulb and also enables pulsing of the light, thus reducing the power consumption further.

The camera may be movably arranged, which is advantageous in that the same camera may be used with all possible optical configurations. This makes manufacture less expensive.

The intermediate optics may comprise at least two intermediate objectives.

The intermediate objectives may have a magnification factor chosen from the group comprising of 0.33, 0.5, 0.66 and 1.

The front optics may comprise at least two end objectives.

The end objectives may have a magnification factor chosen from the group comprising of 10, 20, 40, 50, 63 and 100.

With a suitable choice of intermediate objectives and end objectives an appropriate number of different magnification factors can be achieved for the task for which the analyser is to be used. The combination of intermediate objectives and end objectives makes it possible to use widely used objectives, thus making manufacture less expensive.

The analyser may comprise a focusing lens for focusing the light from the light source.

The focusing lens may have two end portions refracting the light and an intermediate portion there between providing total reflection of the light. With such a focusing lens, sufficient illumination and appropriate numerical aperture may be achieved in a highly economical way. Sufficient illumination and appropriate numerical aperture are important for achieving good resolution and high shutter speeds.

The focusing lens may be essentially circular cylindrical and the end portions may essentially have the shape of spherical segments.

The movement of the robot may be configured to be executed by means of linear actuators.

The movement of the movable parts of the optics is preferably configured to be executed by means of linear actuators.

Linear actuators provide a practical way of achieving the desired movements.

An analyser is provided for optical analysis of a biological specimen, comprising a robot for transporting a slide with a sample to be analysed. The analyser is characterised in that the robot is controlled by at least three motors, to allow movement of the robot in three dimensions, wherein the robot comprises a handling device configured to grip the slide. This is advantageous in that the robot may move the slide in three dimensions, e.g., from a magazine to a microscope.

At least two of said motors may be arranged to move along a respective screw. With a suitable choice of motors and screws, the robot is in itself able to execute both coarse adjustments and fine adjustment, e.g., for focusing to achieve a satisfying image of the sample.

The screw may be stationary, which is advantageous in that the risk of obtaining a critical number of revolutions is eliminated. Also, the moment of inertia radically decreases.

The screw may be fixedly arranged in one of its ends and freely arranged in its other end, which is advantageous in that possible defects in the orientation of the screws in the x,y-plane effects the movement in the z-plane at the smallest extent. Due to the non-fixed arrangement of one end of the screw, the screw will not compete with a guide rail guiding the movement of the robot, and therefore, absolute parallelism between the screw and the guide rail need not be achieved when manufacturing the analyser.

The freely arranged end of the screw may be the one closest to where the optical analysis is performed. This is advantageous in that it is most important to have proper fine motor ability where the optical analysis is performed.

The handling device may be configured to open by means of a motor and to close by means of a spring. This is advantageous in that in case of a power failure, the handling device will not drop the slide, since a spring is holding the slide in place. Also, the handling device can handle variations in the thickness of the glass of the slide.

The handling device may comprise a sensor which is arranged to alert if the handling device is completely closed. This is advantageous in that the sensor will alert the operator if the handling device is completely closed and accordingly not carrying a slide.

BRIEF DESCRIPTION OF THE DRAWINGS

The above, as well as additional objectives, features and advantages of the present invention will be better understood through the following illustrative and non limiting detailed description of embodiments of the present invention, with reference to the appended drawings.

DETAILED DESCRIPTION OF PREFERRED EMBODIMENTS OF THE INVENTION

Figure 1:
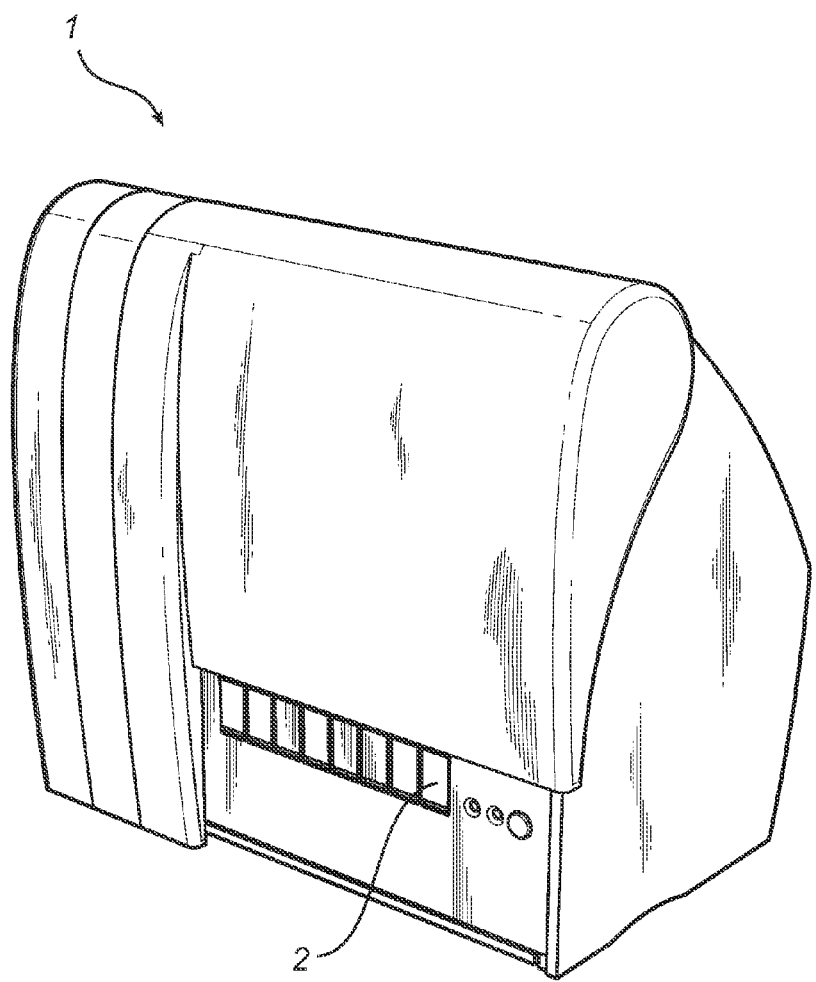
FIG. 1 is a perspective view of an analyser for optical analysis of a biological specimen.

An analyser 1 for optical analysis of a biological specimen is illustrated in FIG. 1. The analyser 1 has cavities 2 where a magazine containing slides can be placed. Each magazine contains a plurality of slides. The analyser 1 may have several cavities 2 to place more than one magazine at a time in the analyser 1. In the embodiment illustrated in FIG. 1, the analyser has eight cavities 2.

Figure 2:
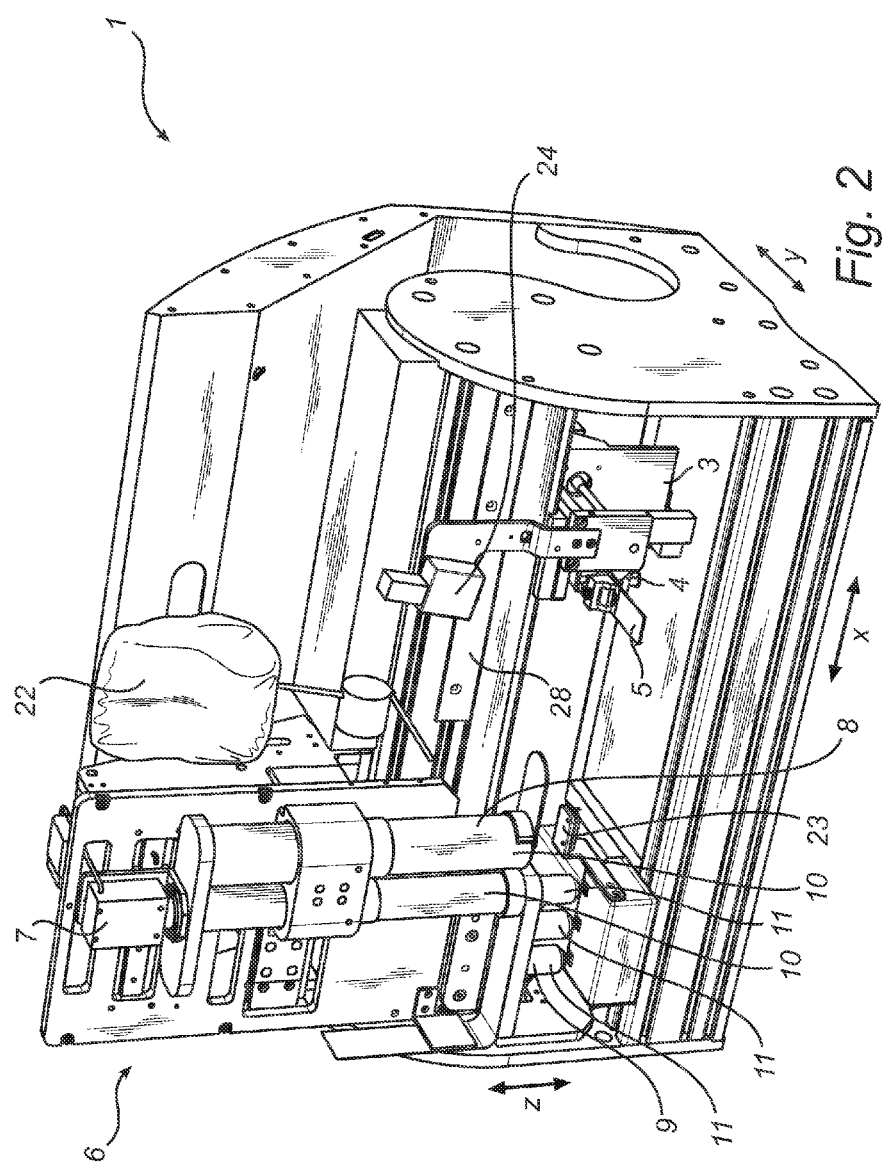
FIG. 2 is a perspective front view of the analyser with the cover removed.

In FIG. 2, the analyser 1 is illustrated with a robot 3. The robot 3 is movably arranged so that it can move along the x-, the y-, and the z-axis. The robot comprises a handling device 4 to grip the slide 5 to be analysed. The handling device 4 is opened by means of a motor and closed by means of a spring. Also, the handling device 4 is equipped with a sensor which alerts if the handling device 4 is completely closed.

The optics 6 in the analyser 1 comprises a camera 7, intermediate optics 8 and front optics 9. The camera 7 is movably arranged so that it can move along the x-axis (double arrow X in FIG. 2) by means of a motor 18 moving along a screw 19 (see FIG. 3). The intermediate optics 8 is movably arranged so that it can move along the x-axis. The movement of the camera 7 as well as the intermediate optics 8 is executed by means of a linear actuator. The intermediate optics 8 comprises two objectives 10. In the example shown, the intermediate objectives have magnification factors 0.5 and 1, respectively. The front optics 9 is fixedly arranged. In the embodiment illustrated in FIG. 2, the front optics has three objectives 11 with magnification factors 10, 40 and 100, respectively. This combination of objectives makes it possible to achieve magnifications of 5, 10, 20, 40, 50 and 100 times, respectively.

In connection with each end objective 11, there is an LED (not shown) for illuminating the smear that is being analysed. The LEDs are movable along the z-axis in order to be able to move them out of the way when a slide 5 that has been analysed is to be removed from the optics 6. In this manner it is possible to avoid that any oil on the slide spills onto the LEDs.

Figure 5:
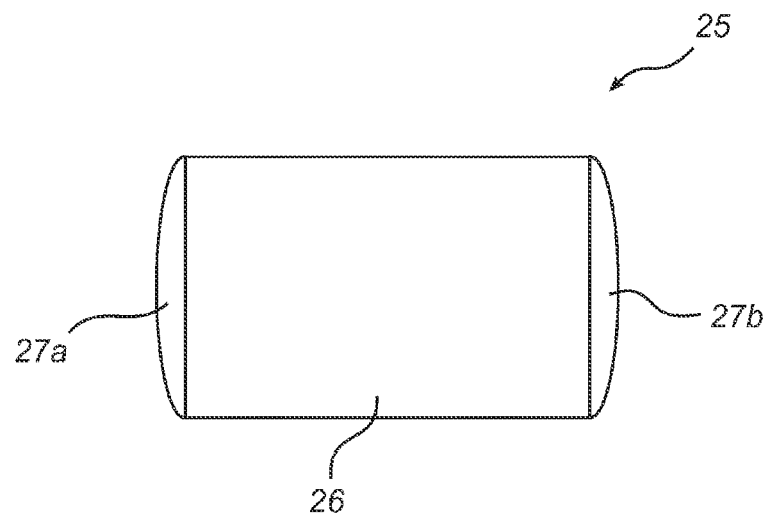
FIG. 5 illustrates a focusing lens.

A focusing lens 25, as shown in FIG. 5, is arranged to focus the light from the LEDs onto the slide, in order to achieve a satisfactory illumination and an appropriate numerical aperture. The focusing lens 25 has an essentially circular cylindrical intermediate portion 26. At each end of the intermediate portion 26 there is an end portion 27, which has the shape of a spherical segment. The light from the LED enters the focusing lens 25 and is refracted by the first end portion 27a. In the intermediate portion 26, the light is totally reflected in the outer surfaces. Before the light exits the focusing lens, it is once again refracted by the second end portion 27b.

Figure 3:
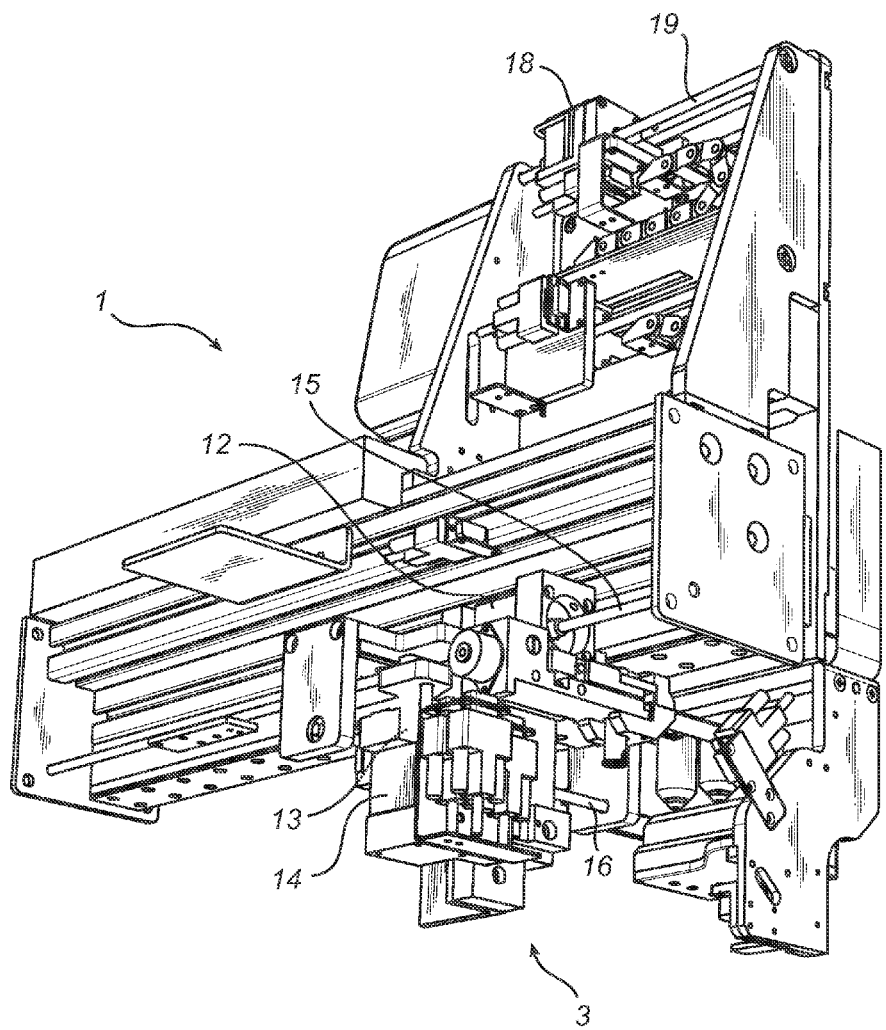
FIG. 3 is a perspective rear view of the analyser showing a robot transporting a slide with a smear to be analysed.

FIG. 3 illustrates the robot 3 which is controlled by three motors 12, 13, 14, two of which 12, 13 are moving along a screw 15, 16, and the third motor 14 moving the slide 5 by means of the screw 17 to achieve movement in three dimensions. To achieve movement along the x-axis the robot has the motor 12 which moves along the screw 15. To achieve movement along the y-axis the robot has the motor 13 (indicated in FIG. 3, but obscured behind motor 14) which moves along the screw 16. To achieve movement of the slide 5 along the z-axis the robot has the motor 14 which moves the slide 5 along the screw 17. Each screw 15, 16, 17, is fixedly arranged in one end and freely arranged in the other end. The freely arranged end of each screw 15, 16, 17, is the one closest to where the optical analysis is performed, i.e. closest to the optics 6. The screws are stationary, which implies that they do not rotate.

Halfway along the length of each screw 15, 16, 17 there is a position sensor (not shown) for ascertaining the position of the robot 3. Similarly, there is a position sensor at the centre of the screws along which the camera 7 and the intermediate optics move. This placement of the sensors in the middle reduces the required number of sensors as compared to arranging one sensor at each end of each screw.

On the analyser 1, a disposable oil bag or oil pack 22 is arranged, containing optical oil. When the oil pack 22 is empty, it may easily be removed and replaced with a new, full oil pack. In order to ensure that each slide is provided with a drop of oil and that the oil pack is not empty, a fork is arranged for sensing drops passing from the oil pack to the slide. A squeegee 23 or sponge may be arranged for removing oil from the slide once it has been analysed before it is returned to the magazine.

Figure 4:
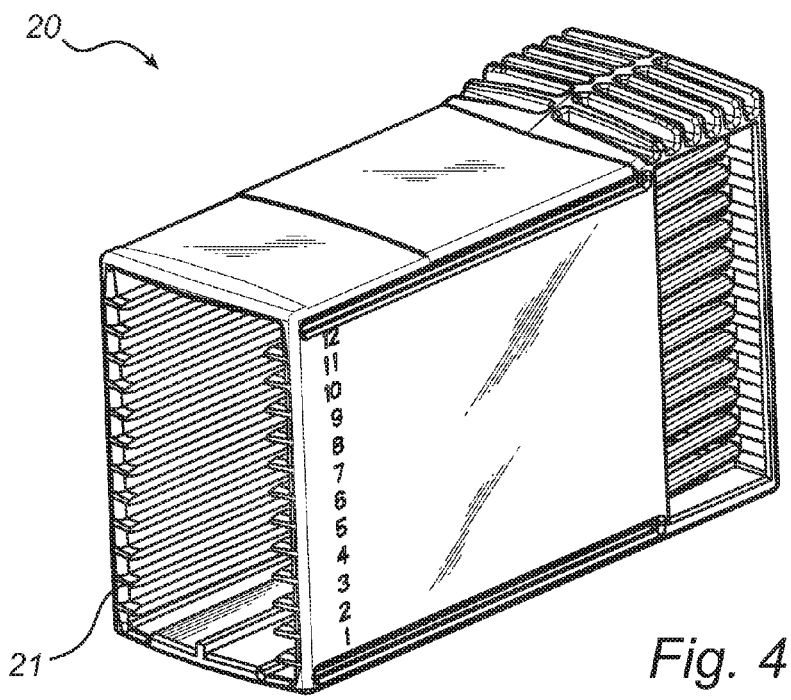
FIG. 4 is a perspective view of a magazine for holding the slides.

In FIG. 4 a magazine 20 for use in the analyser 1 is shown. The magazine has slots 21 for twelve slides arranged in a stack. In each slot 21, there are springs maintaining the slide in position. Thereby, it can be assured that slides do not fall out of the magazine 20, should it be accidentally knocked over or dropped. A correct positioning of the slide in the magazine also makes it easier for the robot 3 to grip the slide.

When analysing a sample in the form of a smear on a slide 5 with the analyser 1, the slide 5, which is stored in the magazine 20 is at first gripped by the handling device 4 and pulled out a bit from the magazine 20. A bar code reader 24 arranged on the main structure beam 28 of the analyser reads a bar code (not shown) on the slide 5 to retrieve information concerning the slide 5. If the slide 5 is to be analysed, the handling device 4 takes a better grip of the slide 5 and the robot 3 transports it to the optics 6 for analysing. By using the objectives 10 in the intermediate optics 8 combined with the objectives 11 in the front optics 9, a number of different magnification factors can be used to create a satisfying image for the operator. Coarse adjustments as well as fine adjustments of the movement of the slide 5, including focus, are executed by means of the robot 3. The camera 7 can take a picture of the smear on the slide 5 and send it to a computer (not shown) where an operator is able to watch the image of the smear on the slide 5. After the analysis, the robot 3 lowers the slide 5 in order to release optical oil placed on the slide from the end objective 11 in order to avoid spilling oil. The LED is also lowered in order to avoid interfering with the downward movement of the slide 5. The robot 3 then transports the slide 5 back to the magazine 20 and puts the slide back in the same slot 21 from where it was pulled out.

The analyser 1 can be used for analysing blood samples, but also for other samples. In general, the analyser 1 is suitable for scanning of all kinds of biological specimens, including, but not limited to blood and bone marrow smears, cytological samples, such as Pap smears, and histopathological tissue sections.

The skilled person realises that a number of modifications of the embodiments described herein are possible without departing from the scope of the invention, which is defined in the appended claims.

For instance, the intermediate optics may also have other magnification factors than the ones described above. Usually, the magnification factors will be chosen from the group consisting of 0.33, 0.5, 0.66 and 1, but other magnification factors are also possible.

Similarly, the front optics may have other magnification factors. The front optics will in most cases have at least two objectives 11 with a magnification factor chosen from the group comprised of 10, 20, 40, 50, 63 and 100. Other magnification factors are also possible. In the embodiment shown, the front optics has three objectives, but it could for instance have only two objectives. These could in such case have magnification factors 20 and 100, respectively.

In the embodiment described above, illumination of the sample is achieved by means of LEDs. In connection with the focusing lens 25 described above, LEDs are the preferred light source. However, in general, other light sources may also be used, such as light bulbs.

An additional slot (not shown) in addition to the slots 2 on the front of the analyser may be used as a reserve slot for receiving single slides that are not placed in a magazine. This is convenient if an emergency sample needs to be analysed. Such a reserve slot also enables a continuous flow in case a robot is used for transferring a slide from, e.g., a smearing device to the analyser without using a magazine. Additionally, the reserve slot can be used as a discharge opening in case of power failure. If a power failure has reset the analyser 1 with the robot 3 holding a slide 5, the robot 3 will not know in which slot 21 in the magazine 20 to return the slide 5 and can instead discharge the slide 5 through the reserve slot.

Another way of solving the problem of handling slides 5 that are held by the robot when there is a power failure is to program the analyser 1 such that the robot 3 remembers where to go with slide 5 and such that, when power is returned, the robot 3 resumes its work where it was interrupted.

In the embodiment shown, the screws along which the motors move are fixedly arranged in the end farthest from the optics and freely arranged in the end closest to the optics. Another way of achieving a freedom of movement near the point of analysis, i.e. near the optics, could be to use a longer screw which is fixed at both ends and to arrange it such that the optics is placed close to the centre of the screw.

In the case of an analyser 1 with only one slot 2 for magazines 20, the bar code reader 24 may be fixedly arranged on the main structure beam 28 of the analyser 1. In the case of an analyser 1 with more than one slot 2 for magazines, such as the embodiment described above, the robot 3 may be arranged to catch the bar code reader 24, such that it slides along the main structure beam 28 accompanying the robot 3 as it moves to the current magazine 24. As the robot 3 moves the slide into the area of analysis, below the optics 6, the bar code reader 24 is left at the first magazine slot 2.

It should be noted that the robot and the optics of the analyser described can be used together in an analyser, but that they can also be used independently of each other.

The invention claimed is:

1. Analyser for optical analysis of a sample, comprising:
optics, including a camera, intermediate optics comprising at least two intermediate objectives, and front optics, the front optics being fixed, the intermediate optics being relatively movable, along a first direction, with respect to the fixed front optics, and the camera being arranged for movement along the first direction of said intermediate optics, wherein the first direction is non-parallel to an optical axis of each of the at least two intermediate objectives, and the front optics comprises at least two end objectives and the camera is arranged for movement independently of the intermediate optics, thereby providing a number of different magnification factors,
wherein each magnification factor is provided by combining only one of the at least two intermediate objectives with only one of the at least two end objectives, and
wherein the at least two intermediate objectives are on a first axis, wherein the at least two end objectives are on a second axis separate from the first axis, wherein the optical axis of each of the at least two intermediate objectives and an optical axis of each of the at least two end objectives are arranged along the imaging direction of the camera.

2. Analyser according to claim 1, wherein the intermediate optics have magnification factors chosen from 0.33, 0.5, 0.66 and 1.

3. Analyser according to claim 1, wherein the end objectives have magnification factors chosen from 10, 20, 40, 50, 63 and 100.

4. Analyser according to claim 1, further comprising at least one light source and a focusing lens for focusing the light from the at least one light source.

5. Analyser according to claim 4, wherein said focusing lens includes two end portions refracting the light and an intermediate portion there between providing total reflection of the light.

6. Analyser according to claim 5, wherein said focusing lens is essentially circular cylindrical and wherein said end portions essentially have the shape of spherical segments.

7. Analyser according to claim 1, wherein the movement of the optics is configured to be executed by way of a linear actuator.

8. Analyser according to claim 4, wherein said at least one light source is a light emitting diode.

9. Analyser according to claim 1, wherein the at least two intermediate objectives have different magnification factors.

10. Analyser according to claim 1, wherein the at least two end objectives have different magnification factors.

11. Analyser according to claim 1, wherein the at least two intermediate objectives are arranged substantially parallel to each other on the first axis, wherein the at least two end objectives are arranged substantially parallel to each other on the second axis.

* * * * *